(12) United States Patent
Taylor (10) Patent No.: US 8,974,401 B2
(45) Date of Patent: Mar. 10, 2015

(54) HELICAL CLIP AND METHOD OF USING THE SAME

(75) Inventor: Kevin D. Taylor, Colorado Springs, CO (US)

(73) Assignee: Syntervention, Inc., Rocky Mount, NC (US)

(*) Notice: Subject to any disclaimer, the term of this patent is extended or adjusted under 35 U.S.C. 154(b) by 342 days.

(21) Appl. No.: 13/367,203

(22) Filed: Feb. 6, 2012

(65) Prior Publication Data

US 2012/0220897 A1 Aug. 30, 2012

Related U.S. Application Data

(60) Provisional application No. 61/446,477, filed on Feb. 24, 2011.

(51) Int. Cl.
*A61M 25/00* (2006.01)
*A61B 19/02* (2006.01)
*A61M 25/09* (2006.01)
*A61B 19/00* (2006.01)

(52) U.S. Cl.
CPC .......... *A61M 25/002* (2013.01); *A61B 19/0256* (2013.01); *A61M 2025/09116* (2013.01); *A61M 2025/09125* (2013.01); *A61B 2019/267* (2013.01)
USPC ....................................................... 600/585

(58) Field of Classification Search
CPC ...................................................... A61M 25/09
USPC ................. 600/250, 374, 473, 585, 549, 595; 607/122, 179; 604/103.09, 523, 528, 604/174, 179, 351; 294/19.1; 224/682, 224/148.5–148.6, 578; 606/1, 113; D8/356; 24/27; 248/75; 137/355.16
See application file for complete search history.

(56) References Cited

U.S. PATENT DOCUMENTS 2,143,440 A * 1/1939 Hitchcock ................ 248/229.26
4,829,999 A 5/1989 Auth
5,125,416 A 6/1992 Phillips
(Continued)

FOREIGN PATENT DOCUMENTS

JP 06-063150 3/1994

OTHER PUBLICATIONS

Item # CIB 30, Small Ceramic Bushing with Helical Wound Clip, Intek Corporation Web Site at http://industrial-ovens.intekcorp.com/item/replacement-parts-for-heaters-and-ovens/ceramic-insulator-bushings/item-1004?&bc=100%7C1005%7C1032, accessed as early as Mar. 23, 2011, 1 page.

*Primary Examiner* — Adam Eiseman
(74) *Attorney, Agent, or Firm* — Aspire IP; Scott J. Hawranek (57) ABSTRACT

The invention relates to a retaining clip for retaining at least one medical line in a shortened lateral position and/or to a supportive surface. In one embodiment, the device includes an elongated, tapered helical wire structure defining a hook shaped leading edge, a loading channel, an inner lumen and a handle on the trailing end. The hooked shaped leading edge, inner lumen and channel are configured to accept the largest diameter of medical wires the device is destined to be used with. Sections of the medical wire may be captured in the hook portion, and multiple rotations of the structure by the handle, moves the medical wire(s) into the channel and the inner lumen to be retained.

17 Claims, 5 Drawing Sheets

(56) References Cited

U.S. PATENT DOCUMENTS

| | | |
|---|---|---|
| 5,364,355 A | 11/1994 | Alden et al. |
| 5,666,968 A | 9/1997 | Imran et al. |
| 6,139,540 A | 10/2000 | Rost et al. |
| 6,231,564 B1 | 5/2001 | Gambale |
| 6,247,211 B1 * | 6/2001 | Bell .................. 24/306 |
| 6,290,691 B1 | 9/2001 | Krieger |
| 6,618,540 B2 * | 9/2003 | Wu et al. ................ 385/137 |
| 6,648,279 B1 * | 11/2003 | Malin et al. .............. 248/65 |
| 7,229,431 B2 * | 6/2007 | Houser et al. ............ 604/103.04 |
| 7,413,153 B1 * | 8/2008 | Ghormley ................ 248/229.2 |
| 7,527,606 B2 * | 5/2009 | Oepen ................ 604/103.04 |
| 7,798,980 B2 * | 9/2010 | Melsheimer ................ 600/585 |
| 8,075,497 B2 * | 12/2011 | Melsheimer ................ 600/585 |
| 8,147,102 B1 * | 4/2012 | Townes ................ 362/396 |
| 2002/0183733 A1 * | 12/2002 | Mulier et al. ................ 606/28 |
| 2008/0009883 A1 | 1/2008 | Bieneman |
| 2008/0084076 A1 | 4/2008 | Van Sloun |
| 2008/0264993 A1 | 10/2008 | Schulte et al. |

* cited by examiner

HELICAL CLIP AND METHOD OF USING THE SAME

This application claims the benefit of U.S. Provisional Patent Application No. 61/446,477, filed on Feb. 24, 2011, which is hereby incorporated by reference for all purposes as if fully set forth herein.

BACKGROUND OF THE INVENTION

1. Field of the Invention

The invention relates to retaining clips and, more specifically, retaining clips for securing medical devices, such as, medical lines, catheters, guidewires, electrical lines, tubing, cables, and other elongated members.

2. Discussion of the Related Art

Guidewires and catheters are used in a variety of different medical procedures, for example during angiographic, endovascular, or surgical procedures. Guidewires are typically used to position catheters in a body lumen, for example arteries, veins or natural orifices within a mammal. The leading end portion of the guidewire is typically introduced into the body through an incision or natural orifice and then advanced to the treatment area. A catheter can be threaded over the guidewire, and advanced over the guidewire to the treatment area. A single guidewire can be used to deliver multiple catheters to the treatment area within the body lumen. This is normally accomplished by withdrawing and removing the first catheter from the wire while leaving the leading edge of the wire in place within the body lumen, and then threading a second catheter over the wire and advancing down to the treatment site. Multiple guidewires and catheters can be inserted into the body lumen at the same time.

When the guidewire or a guidewire and catheter combination is placed within the body lumen, a loose trailing end portion extends out of the patient from the entry point. This trailing end portion can be difficult to manage and requires special attention from the medical staff to ensure it does not become contaminated, tangled or confused with other wires in the procedural area. Much of this difficulty comes from the length of the guidewires and catheters that can range from about 1 foot to about 10 feet or more. Furthermore, these devices can be very small in diameter, making them very difficult to see and pick up, and are commonly made of stiff, springy materials that resist being looped or coiled into a shorter configuration. When bent, there is always the possibility one end will become free and the device will spring uncontrollably and touch a non-sterile surface. Once the device contacts a non-sterile surface, it is contaminated and must be replaced.

When the catheters and guidewires are removed from the body they are typically placed on a small sterile table in case they are needed later in the procedure. Since the table is much shorter than the devices, the catheters and wires are either placed back into the package they were delivered in, or manually coiled up with the ends wrapped around the coil to keep the coil from springing open. Alternatively, sterile gauze or tape may be wrapped around the coil, or a sterile towel may be placed on top of the coiled device. Placing the device back into the package can be difficult, time consuming and often damages the wire or catheter. Manually coiling and wrapping the device around the coil can damage the catheter or wire, and may produce a configuration that must be untangled when it is needed again for the procedure. Further, there is always the possibility of the coil unraveling and springing from the sterile area. Using sterile gauze, tape, or towels to hold the coil has a high potential of lint or other contaminations being deposited into the device and has limited effectiveness.

Therefore, a device and method for retaining a medical line in a shorter lateral length and/or to a supportive surface is needed.

SUMMARY OF THE INVENTION

Accordingly, this invention is directed towards a retention device and method of using the same that substantially obviates one or more of the problems due to limitations and disadvantages of the related art.

An advantage of the invention is to provide an apparatus to securely retain a medical wire to a medical surface while providing ease of loading and removal of the medical wire from the apparatus.

Yet another advantage of the invention is to provide a simple and secure mechanism to attach an apparatus to a surface.

Another advantage of the invention is to provide a very versatile, effective, easy to use, and economical solution for securing medical devices in a shortened lateral length or to a supporting surface. With a few twists of the handle, a medical device is securely retained within the retention device.

Yet another advantage of the invention is to provide a retention device configured to be operable with only one hand.

Still yet another advantage of the invention is to provide a retention device that may secure a medical instrument in a couple seconds.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages, and in accordance with the purpose of the invention as embodied and broadly described, an aspect of the invention is directed towards a retaining clip device for retaining at least one medical device in a shortened lateral position and/or to a supportive surface. The device includes a unitary helical structure including a hook shaped leading edge, a loading channel, an inner lumen and a handle on a trailing end. The hooked shaped leading edge, inner lumen and channel are configured to accept a portion of the medical device upon rotation of the handle.

Another aspect of the invention is directed towards a method of using a retaining device to secure a portion of a medical device. The method includes aligning an opening of the retaining device to a position adjacent to the medical device. Next, rotating the retaining device to capture a portion of the medical device in a channel of the retaining device. The rotation includes at least two revolutions of the retaining device.

Yet another aspect of the invention is directed towards a kit. The kit includes a retaining device according to any embodiment of the invention and instructions for use. The kit may also include a secondary medical device, e.g., stent, catheter and the like.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide further understanding of the invention, are incorporated in and constitute a part of this specification. They illustrate embodiments of the invention and together with the description serve to explain the principles of the invention.

In the drawings.

FIG.. 4 is a perspective view of the retaining clip of FIG.. 1 with a medical device in second configuration.

DETAILED DESCRIPTION OF THE ILLUSTRATED EMBODIMENTS

An aspect of the invention is directed towards a retaining clip for retaining at least one medical device, e.g., medical line in a shortened lateral position and/or to a supportive surface.

In one embodiment, the retaining clip includes an elongated, tapered helical wire structure defining a hook shaped leading edge, a loading channel, an inner lumen and a handle on the trailing end. The hooked shaped leading edge, inner lumen and channel are designed to accept the largest diameter of medical device destined to be used with. More specifically, a section or sections of the medical device may be captured in the hook portion and multiple rotations of the retaining clip. For example, rotation of the handle coupled to the retaining clip rotates a hook portion of the retaining clip to capture a portion of the medical device into the channel and the inner lumen to be retained.

In one embodiment, the invention is directed towards a retaining clip device for retaining at least one medical device in a shortened lateral position and/or to a supportive surface. The device includes a unitary helical structure including a hook shaped leading edge, a loading channel, an inner lumen and a handle on a trailing end. The hooked shaped leading edge, inner lumen and channel are configured to accept a portion of the medical device upon rotation of the handle.

In one embodiment, the invention is directed towards a method of using a retaining device to secure a portion of a medical device. The method includes aligning an opening of the retaining device to a position adjacent to the medical device. Next, rotating the retaining device to capture a portion of the medical device in a channel of the retaining device. The rotation includes at least two revolutions of the retaining device.

In one embodiment, the invention is directed towards a kit. The kit includes a retaining device according to any embodiment of the invention and instructions for use. The kit may also include a secondary medical device, e.g., stent, catheter and the like.

In one embodiment, wherein the unitary helical structure includes a wire made of materials such as a plastic, thermoplastic, plastic monofilament nylon, polytetrafluoroethylene (PTFE), fluorinated ethylene propylene (FEP), PET, polyvinylidene fluoride (PVDF), metal, steel, stainless steel, nitinol, titanium plastic coated metal wire, combinations of the same and the like. In a preferred embodiment, the wire has a diameter of about 0.01 inches to 0.08 inches or greater.

In one embodiment, the pitch of the helical structure varies along its length.

In one embodiment, the helical wire cross section is round, rectangular, non-linear with combinations of the same.

In one embodiment, the loading channel has a pitch in a ranging from about 1 to about 25 times the wire diameter.

In one embodiment, the handle comprises windings of equal diameter.

In one embodiment, the retaining device is coupled to a secondary attachment mechanism coupled to a handle of the retaining device, e.g., a releasable spring clip.

In one embodiment, the retaining device is coupled to a mass unit and the mass unit is coupled to the handle. The mass unit is a weighted structure having a mass in a range from about 3 grams to about 250 grams or greater.

In one embodiment, a supportive structure is arranged over a portion of the handle. The supportive structure may include ergonomic features to aid in gripping of the handle, such as a soft or textured surface. The handle may also have a hook or non-linear feature coupled to or integral with the trailing end of the handle. The hook may be configured to connect to a supporting surface, or for reducing the lateral length of the medical line.

Reference will now be made in detail to an embodiment of the present invention, example of which is illustrated in the accompanying drawings.

Figure 1:
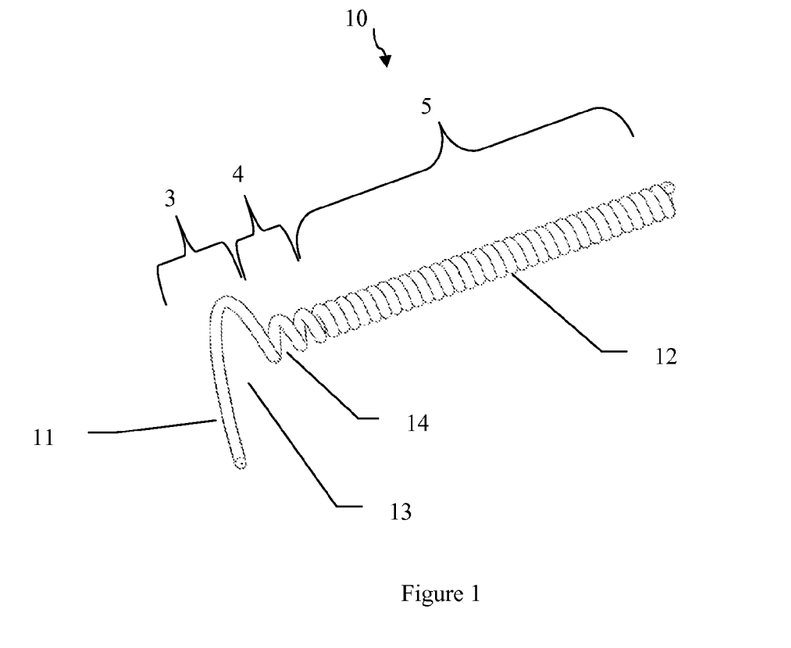
FIG. 1 is a perspective view of the retaining clip according to an embodiment of the invention.
Figure 2:
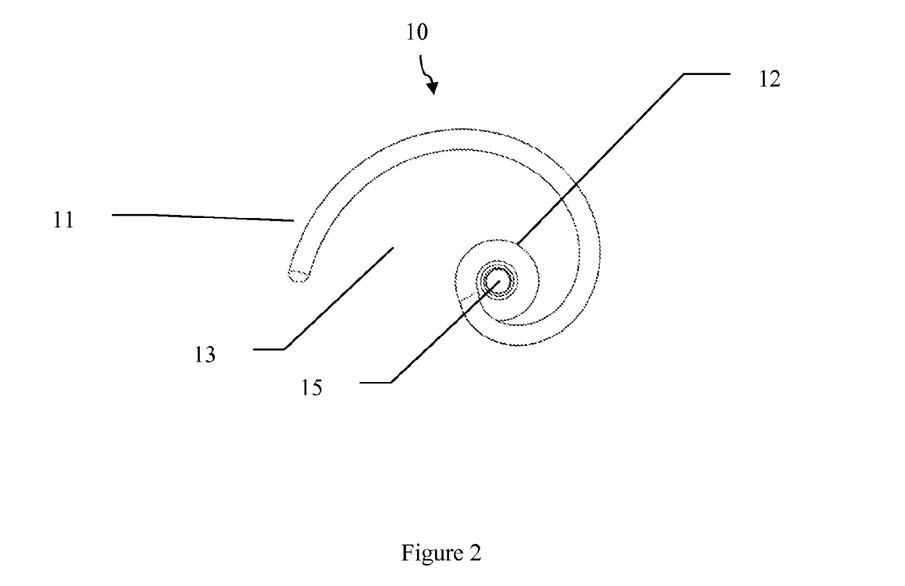
FIG. 2 is a front view of the retaining clip of FIG.. 1.

FIG. 1 is a perspective view of the retaining clip according to an embodiment of the invention. FIG. 2 is a front view of the retaining clip of FIG. 1.

Referring to FIGS. 1 and 2, a retaining clip 10 is configured to retain a medical device, e.g., a medical line, in a shorter lateral length and/or to a supportive surface. In this embodiment, the retaining clip 10 is an elongated helix wire structure. The helical structure includes three distinct integral sections a first section 3, a second section 4, and third section 5. The first section 3 is configured as a conical helix tapering from the large diameter at leading edge 11 to a smaller diameter. The second section 4 is configured to a distance from the leading edge 11 and includes a conical helix that tapers from the second diameter to a third diameter. The second diameter is larger than the third diameter. A third section 5 is configured as a cylindrical helix at a constant diameter and is configured as a handle 12. The helix has a variable pitch over the length of the structure.

The first section 3, the pitch starts out at a first distance at the leading edge 11 and gradually reduces to a second pitch over the length of the first section. The second section 4 starts out with the second pitch dimension and reduces to a third pitch dimension over its length. In the third section 5, the pitch is constant over the cylindrical helix and defines a handle 12. In this embodiment, the pitch is about the same as the diameter of the helical wire. The abrupt taper and wire pitch in the first section 3 defines a hook shaped opening 13 between leading edge 11 and the handle 12. The hook shaped opening 13 is dimensioned to be larger than the largest medical device, e.g., medical line or bundle of lines, the device is configured to be used with. The pitch and diameter of the helical wire defines the size of the loading channel 14. Inner diameter 15 is also configured to accept a medical device, e.g., a medical line or bundles of medical lines.

Figure 3:
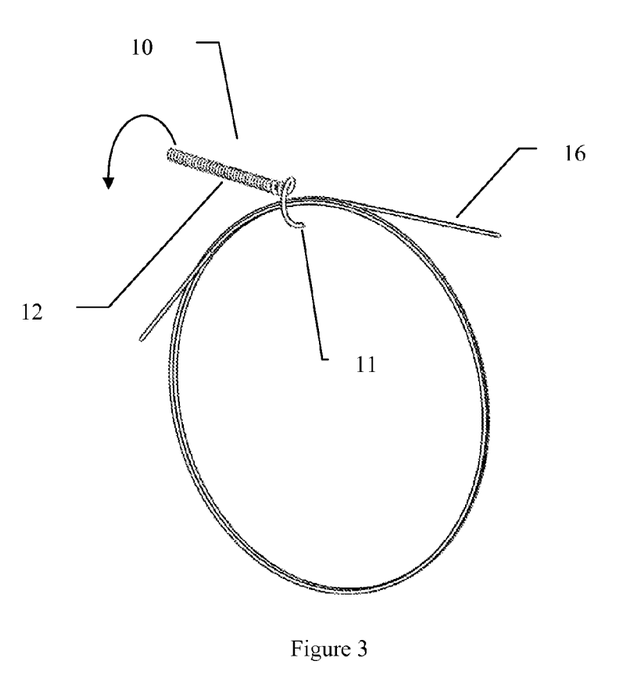
FIG. 3 is a perspective view of the retaining clip of FIG.. 1 with a medical device in first configuration.
Figure 4:
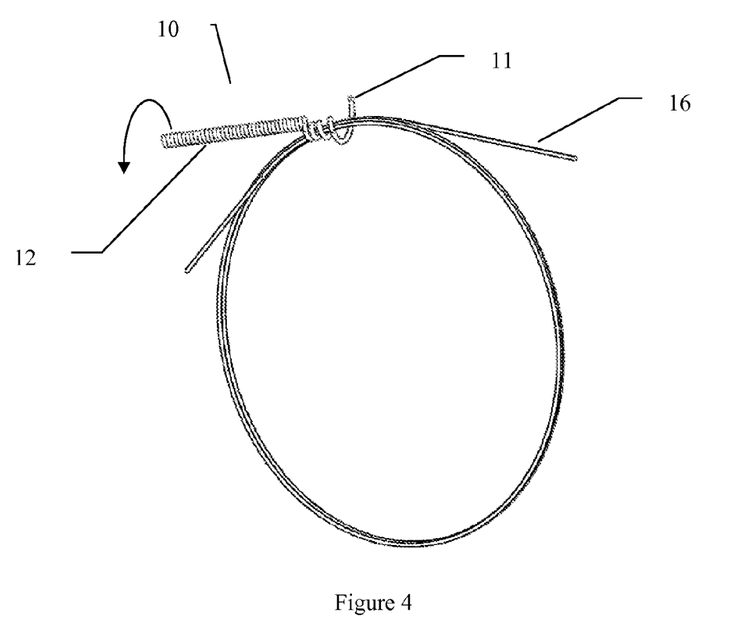

FIG. 3 is a perspective view of the retaining clip of FIG. 1 with a medical device in a first configuration. FIG. 4 is a perspective view of the retaining clip of FIG. 1 with a medical device in a second configuration.

Referring to FIGS. 3 and 4, the retaining clip 10 is placed next to a coiled loop of a medical line 16 so that line is within hooked shaped opening 13. The handle 12 is turned by hand clockwise and line 16 moves into channel 14. As the handle 12 continues to rotate the helical wire is wrapped about the medical line and retains it in a shorter lateral length configuration as shown in FIG. 4. In this embodiment, only one rotation of the retaining device 10 is required to secure the line 16 as the helical wire completely encircles the medical line 16. As more rotations are conducted the medical line 16 is further secured. That is, the decreasing pitch and diameter of the helical puts pressure on the medical line 16 and prevents it from springing open. To release the retaining device from the medical line 16 the handle is simply rotated counterclockwise and the helical wire unwraps from the medical line 16.

Referring to FIG. 4, the retention of the medical line 16 via rotation causes the helical structure surrounding the medical line 16 to offset from the handle section. That is, the helical structure is configured with proper flexibility, diameter and correct pitch to achieve this offset. In one embodiment, these features may be achieved the properties set forth in Table 1. Table 1 includes a chart of dimensions that are configured to provide a good offset when using stiff nylon monofilament, e.g., a small version works well for small guidewires while a medium size works for larger guidewires, e.g., about 0.033 inches to about 0.039 inches, and larger size for larger guidewires or catheters, tubes, e.g., up to about 0.2 diameters and greater. If the pitch or diameter is too small or the wire too stiff it may not accept and/or damage the medical line 16.

TABLE 1

| Small | .033 dia. Mono | | Medium | .036 dia. Mono | | Large | .040 dia. Mono | |
|---|---|---|---|---|---|---|---|---|
| Height | ID | Pitch | Height | ID | Pitch | Height | ID | Pitch |
| 0 | 0.82 | 0.2 | 0 | 0.96 | 0.3 | 0 | 0.96 | 0.4 |
| 0.09 | 0.085 | 0.05 | 0.25 | 0.16 | 0.05 | 0.21 | 0.26 | 0.07 |
| 0.22 | 0.048 | 0.034 | 0.5 | 0.055 | 0.037 | 0.7 | 0.062 | 0.041 |
| 2.5 | 0.048 | 0.034 | 3.2 | 0.055 | 0.037 | 4 | 0.062 | 0.041 |

Figure 5:
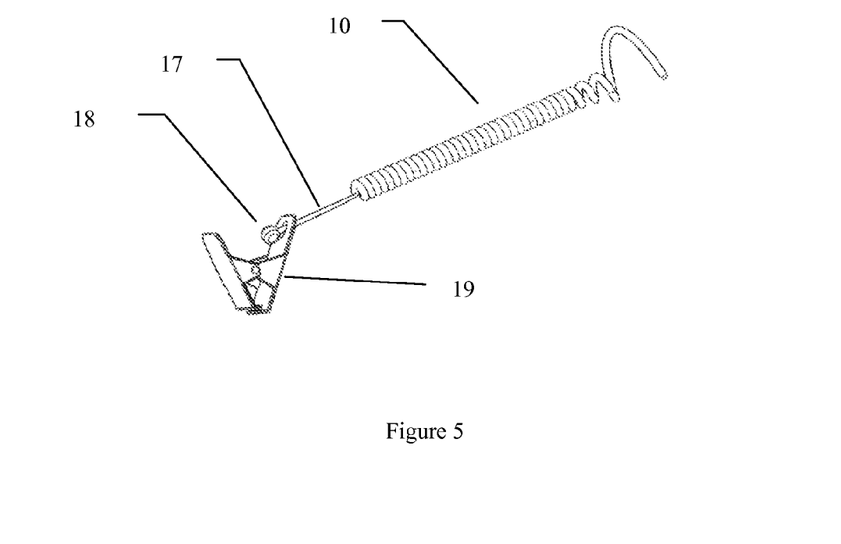
FIG. 5 is a perspective view of another embodiment of the invention.

FIG. 5 shows another embodiment of the invention. Referring to FIG. 5, retaining clip 10 is connected to a common spring clip 19 for securing the medical device 16 (not shown) to a supportive surface such as a surgical drape, bed sheet or gown. Spring clip 19 is attached to retaining clip 10 by a connection unit 17, such as a wire, extending from the retaining clip 10. In this embodiment, the wire passes coupled to an internal section of the spring clip 19 and releasably coupled to the spring clip 19. This coupling or attachment may be done with various techniques, such as, heating to form a ball end 18 with a diameter larger than a hole in the spring 19, crimping an end portion of the connection 17, adhesives, molded plastics, knots and/or combinations of the same and the like.

In one embodiment, the medical wire 16 is secured in the retaining clip 10 as described previously with reference to FIGS. 3-4 and the spring clip handles are pressed to open the jaws of the clip. A section of the supporting surface, e.g., sheet, drape or gown is placed between the open jaws and the pressure on the handle is released, and the jaws spring shut around the fabric, securing the retaining clip 10 and medical wire 16 to the supporting surface. Spring clip 19 is just one example of an attachment mechanism configured to secure a retaining clip to a supportive surface. Other mechanisms as known in the art could also be employed, such as a pressure sensitive adhesive pad which could be attached to a retaining clip 10 for securing to a supportive surface.

Figure 6:
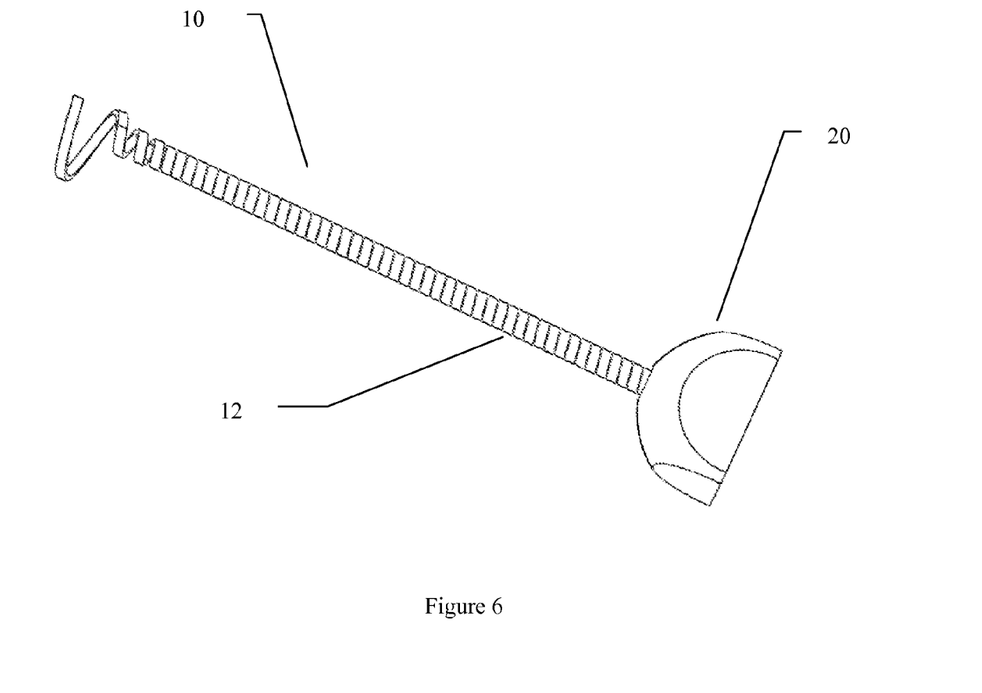
FIG. 6 is a perspective view of another embodiment of the invention.

FIG. 6 is a perspective view of another embodiment of the invention.

Referring to FIG. 6, the retaining clip 10 includes a helical wire having a rectangular cross section coupled to a mass unit 20 secured to the handle 12. The mass unit 20 or mass is conical shaped with square edges formed on the periphery and has a hole drilled in it sized to accept handle 12 of retaining clip 10. The mass 20 is attached to retaining clip 10 with a suitable adhesive or other attachment mechanism, e.g., heating, welding, soldering, and the like. The purpose of the mass 20 is to provide extra weight to the retaining clip 10 containing medical line 16, thereby further reducing the possibility of it moving from the sterile area. In a preferred embodiment, the mass unit has a weight in range from about 3 grams to about 250 grams or greater. The mass unit may have any geometric configuration.

Figure 7:
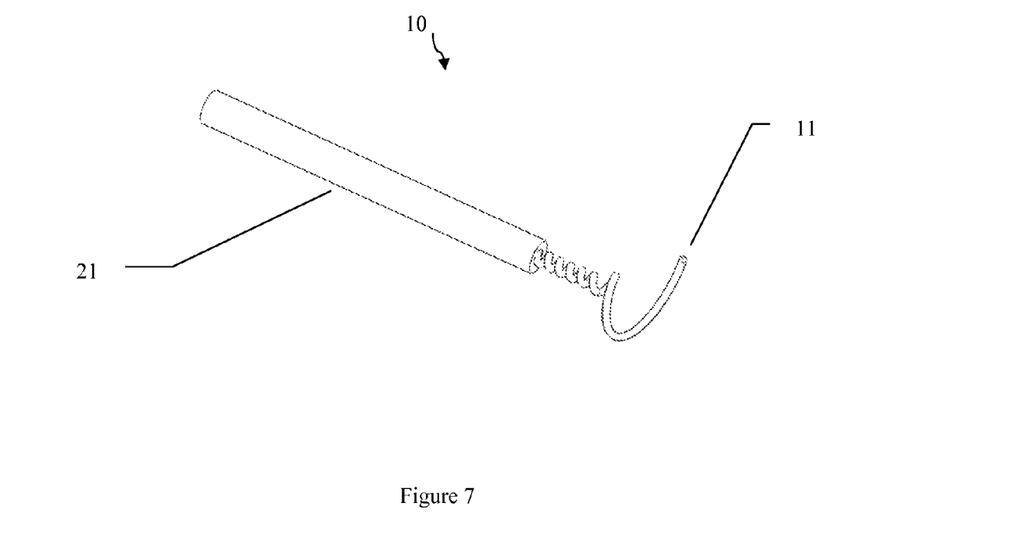
FIG. 7 is a perspective view of another embodiment of the invention.

FIG. 7 is a perspective view of another embodiment of the invention.

Referring to FIG. 7, the retaining clip 10 includes a supportive structure 21, e.g., tubular structure, placed over the handle 12. Tubular structure 21 has an inside diameter close to the diameter of the handle 12 and may be attached with, adhesives, press fit attachments, heat shrinking, welding, insert molding and/or combinations thereof and the other mechanisms as known in the art. The tubular structure 21 provides a platform for rotating the handle, providing a positive stop once the medical line contacts the handle, such that further rotation is prevented when rotating the helical clip over the medical line, and if made with a soft elastomeric material, it can provide extra friction to the medical line to better retain it within the clip. The tubular structure may include ergonomic features, such as, finger grooves, soft or textured surface and the like. Alternatively, the supportive structure can be a plastic or metal rod or tube placed in the inside diameter (ID) of the handle and secured in place by conventional, e.g., an adhesive, heat weld, screw threads, combinations of the same and the like.

Figure 8:
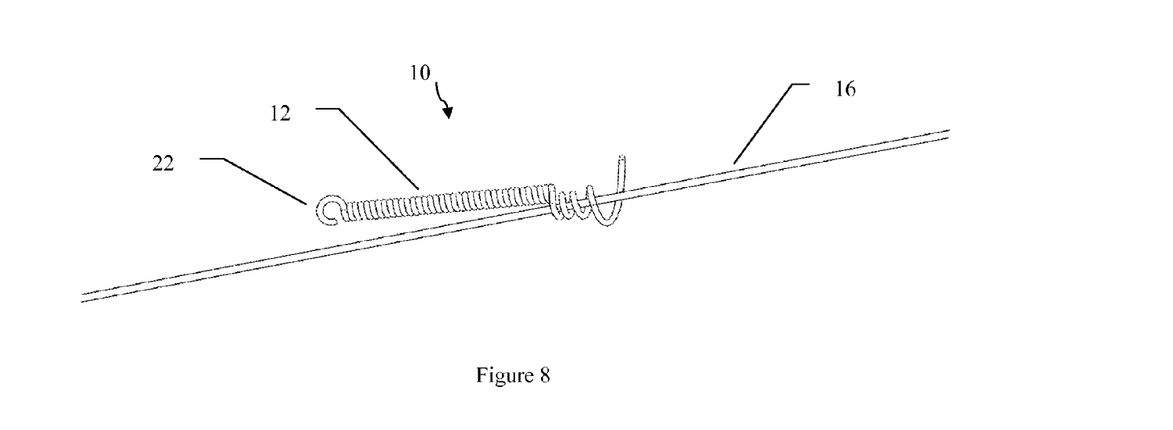
FIG. 8 is a perspective view of another embodiment of the invention.

FIG. 8 is a perspective view of another embodiment of the invention.

Referring to FIG. 8, the retaining clip 10 has an integral hook 22 formed on the trailing end of the handle 12. The hook 22 is semicircular or has a helix shape formed generally parallel to the axis of the handle 12. The hook 22 can be used to shorten the lateral length of a medical line or to attach the retaining clip 10 to a supportive surface, such as another medical line 16. It can also be used as a way to attach to another retaining clip 10 or another device such as a spring clip or a pressure sensitive adhesive pad for securing to a supporting surface.

Figure 9:
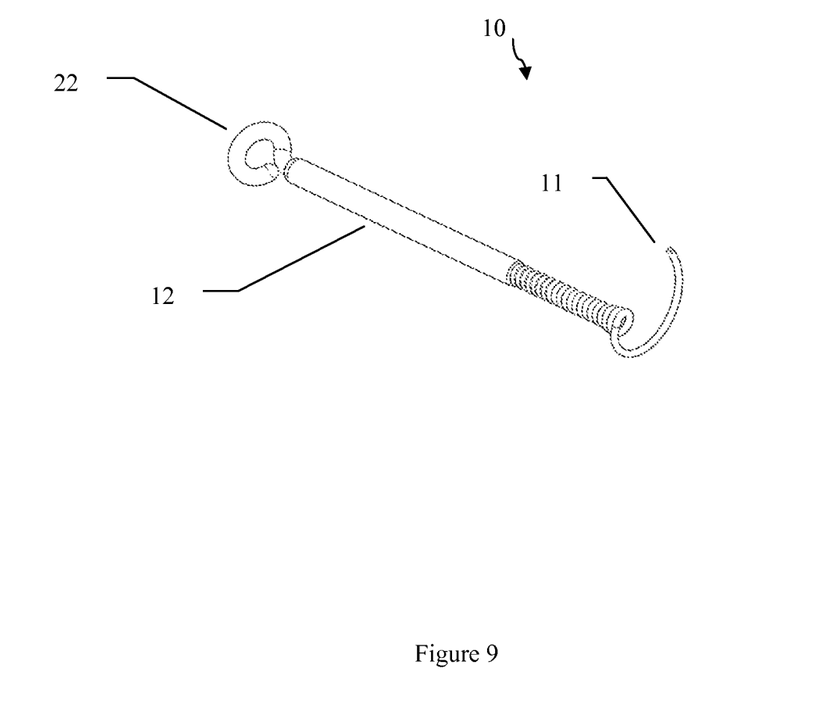
FIG. 9 is a perspective view of another embodiment of the invention.

FIG. 9 is a perspective view of another embodiment of the invention.

Referring to FIG. 9, the retaining clip 10 has a solid handle 12 attached the trailing end of the unitary helical structure. The solid handle overlaps at least a portion of the trailing edge. The leading end of the handle has a nipple end sized to fit within the ID of the helical structure and is attached by adhesive, heat weld, solvent bond, screw threads, combinations and the like. The handle can be made of metal or plastic using conventional forming, molding, or machining processes. The handle is preferably injection molded out of a suitable plastic or thermoplastic, e.g., acrylonitrile butadiene styrene (ABS), styrene, nylon, high-density polyethylene (HDPE), polyethylene terephthalate (PETG), polypropylene (PP), hytrel, elastomer, e.g., pebax, combinations and the like.

Optionally, the handle may include a hook 22 or other supplemental attachment mechanism on the trailing end as described with reference to FIG. 8. Alternatively, the handle may molded inside an inside diameter (ID) of the trailing edge.

EXAMPLES

Without intending to limit the scope of the invention, the following examples illustrate how various embodiments of invention may be made and/or used.

Example 1

In this example, a retaining clip including a unitary helical structure was formed from a nylon monofilament wire having a diameter of about 0.033. The nylon monofilament wire includes a shaped leading edge, a loading channel, an inner lumen and a handle on a trailing end. The shaped leading edge was formed into a hooked shaped leading edge, inner lumen and channel configured to accept a portion of the medical device upon rotation of the handle.

The hooked shaped leading edge (Section 3 of FIG. 1) is about 0.09 inches in length with an inside diameter that tapers from about 0.82 inches to about 0.085 inches. The pitch at the leading edge starts at about 0.2 inches and reduces to about 0.05 inches at the other end. The next section (Section 4 of FIG. 1) is about 0.13 inches in length and has an inside diameter that tapers from 0.085 inches to 0.048 inches and the pitch tapers from 0.050 inches to 0.034 inches. The handle is about 2.3 inches in length and has a constant inside diameter of about 0.048 inches and pitch of about 0.034 inches.

The entire length of the device is about 2.5 inches. The material is about 0.033 inches in diameter made of stiff nylon monofilament described, as Heavy shock tippet, 60 lb test monofilament from Rio Products, of Idaho Falls, Id.

In this Example, the device was formed by first machining a tapered metal mandrel with the before mentioned diameters and tapers. Grooves were machined in making Sections 3 and 4 (shown in FIG. 1) to approximate the variable pitch in those Sections. The monofilament was wound around the mandrel and was heat treated with a hot air gun at a temperature of about 250° F. for about 30 seconds and then allowed to cool for over 30 seconds. After cooling the monofilament was removed from the mandrel and it retains the wound helical shape imparted from the mandrel. Next, a silicone tubing measuring about 1/16 ID inches and 1/8 OD inches was cut to a length of about 2.2 inches and expanded using the appropriate solvent. The expanded tube was then placed over the handle portion and allowed to returns to its original size (after solvent evaporation), thereby firmly attaching the handle to the monofilament.

The inventions and methods described herein can be viewed as a whole, or as a number of separate inventions that can be used independently or mixed and matched as desired. All inventions, steps, processes, devices, and methods described herein can be mixed and matched as desired. All previously described features, functions, or inventions described herein or by reference may be mixed and matched as desired.

It will be apparent to those skilled in the art that various modifications and variations can be made in the present invention without departing from the spirit or scope of the invention. Thus, it is intended that the present invention cover all of the modifications and variations of this invention provided they come within the scope of the appended claims and their equivalents.

What is claimed is:

1. A retaining clip device for retaining at least one medical device, comprising:
   a unitary helical structure including three distinct integral sections comprising a first section, a second section and a third section, the unitary helical structure comprising a first material,
   the first section comprising a leading edge extending to the second section in a tapered conical helix configuration, the leading edge including a first pitch that decreases to a second pitch over a length of the first section, the first pitch is greater than the second pitch,
   the second section starting at an end of the first section and extending to the third section in a tapered conical helix configuration, a start of the second section including the second pitch that decreases to a third pitch over a length of the second section, the second pitch is greater than the third pitch,
   the third section starting at an end of the second section and extending to an end of the third section in a cylindrical helix at the third pitch, the third pitch is constant over the length of the third section; and
   a handle arranged on a portion of the third section the handle comprises a second material different than the first material, wherein a leading edge of the first section is configured to accept a portion of the at least one medical device and the second section is configured to secure the at least one medical device upon rotation of the handle.

2. The device of claim 1, wherein the first pitch of the first section is dimensioned to be larger than the at least one medical device.

3. The device of claim 1, wherein the medical device comprises at least one of a guide wire, a catheter, an electrical line, a cable, and tubing.

4. The device of claim 1, wherein the at least one medical device comprises a coiled guide wire.

5. The device of claim 1, wherein the unitary helical structure comprises a wire.

6. The device of claim 5, wherein the wire has a diameter in a range from 0.01 inches to 0.08 inches.

7. The device of claim 5, wherein the unitary helical structure comprises a material selected from the group consisting of plastic, nylon, a polytetrafluoroethylene (PTFE), fluorinated ethylene propylene (FEP), PET, polyvinylidene fluoride (PVDF), metal, steel, stainless steel, nitinol, and titanium.

8. The device of claim 1, further comprising a secondary attachment mechanism coupled to the handle.

9. The device of claim 8, wherein the secondary attachment mechanism comprises a spring clip.

10. The device of claim 1, further comprising a mass unit coupled to the handle.

11. The device of claim 1, wherein the handle further comprising an ergonomic feature.

12. The device of claim 11, wherein the handle is coupled to an inside diameter (ID) of the trailing edge.

13. The device of claim 1, further comprising a hook on a trailing end of the handle.

14. The device of claim 1, wherein the helical structure comprises a non- circular cross-section.

15. A kit, comprising:
   a retaining device for securing a medical device, comprising:
   a unitary helical structure including three distinct integral sections comprising a first section, a second section and a third section, the first section comprising a leading edge extending to the second section in a tapered conical helix configuration, the leading edge including a first pitch that decreases to a second pitch over a length of the first section, the first pitch is greater than the second pitch, the second section starting at an end of the first section and extending to the third section in a tapered conical helix configuration, a start of the second section including the second pitch that decreases to a third pitch over a length of the second section, the second pitch is greater than the third pitch, the third section starting at an end of the second section and extending to an end of the third section in a cylindrical helix at the third pitch, the third pitch is constant over the length of the third section, and wherein a portion of the first section is configured to accept the medical device and the second section is configured to secure the medical device upon only one rotation of the retaining device in a clockwise fashion and when rotated counter clockwise the medical device is released;

a handle comprising a thermoplastic material coupled to a portion of the third section; and instructions for use.

16. The kit of claim 15, further comprising a secondary medical device.

17. A retaining clip device for retaining a portion of a medical device, comprising:

a unitary helical structure including three distinct integral sections comprising:

a first section;

a second section; and a third section, wherein the first section comprises a leading edge extending to the second section in a tapered conical helix configuration, wherein the leading edge comprises a first pitch that decreases to a second pitch over a length of the first section, wherein the first pitch is greater than the second pitch, wherein the second section starting at an end of the first section and extending to the third section in a tapered conical helix configuration, a start of the second section including the second pitch that decreases to a third pitch over a length of the second section, wherein the second pitch is greater than the third pitch, wherein the third section starting at an end of the second section and extending to an end of the third section in a cylindrical helix at the third pitch, wherein the third pitch is constant over the length of the third section, and wherein a portion of the first section is configured to accept the medical device and the second section is configured to secure the medical device upon only one rotation of the retaining device; and a handle comprising a thermoplastic material arranged on a portion of the third section.

* * * * *